United States Patent
Rong et al.

(10) Patent No.: US 11,525,797 B2
(45) Date of Patent: Dec. 13, 2022

(54) METHOD FOR DETECTING AN AIR DISCHARGE DECOMPOSED PRODUCT BASED ON A VIRTUAL SENSOR ARRAY

(71) Applicant: Xi'an Jiaotong University, Xi'an (CN)

(72) Inventors: Mingzhe Rong, Xi'an (CN); Aijun Yang, Xi'an (CN); Xiaohua Wang, Xi'an (CN); Jifeng Chu, Xi'an (CN)

(73) Assignee: Xi'an Jiaotong University, Xi'an (CN)

( * ) Notice: Subject to any disclaimer, the term of this patent is extended or adjusted under 35 U.S.C. 154(b) by 903 days.

(21) Appl. No.: 16/261,768

(22) Filed: Jan. 30, 2019

(65) Prior Publication Data
US 2020/0240940 A1 Jul. 30, 2020

(51) Int. Cl.
*G01N 27/12* (2006.01)

(52) U.S. Cl.
CPC ......... *G01N 27/122* (2013.01); *G01N 27/128* (2013.01)

(58) Field of Classification Search
CPC ... G01N 27/122; G01N 27/128; G01N 33/034
See application file for complete search history.

(56) References Cited

U.S. PATENT DOCUMENTS

2015/0323510 A1* 11/2015 Huynh ............... G01N 33/0031
73/23.34

FOREIGN PATENT DOCUMENTS

DE 102016222243 A1 * 5/2018
KR 20100119057 A * 11/2010

OTHER PUBLICATIONS

Wei et al., Development of a LeNet-5 Gas Identification CNN Structure for Electronic Noses (Year: 2019).*

* cited by examiner

*Primary Examiner* — Feba Pothen
(74) *Attorney, Agent, or Firm* — Dragon Sun Law Firm, PC; Jinggao Li; Nathaniel Perkins

(57) ABSTRACT

Embodiments of the present disclosure relate to a method for detecting an air discharge decomposed product based on a virtual sensor array, comprising: fabricating a virtual sensor array; disposing the virtual sensor array in a hermetically sealed gas chamber, energizing, and initializing; performing gas-sensitive testing to the virtual sensor array and storing a testing result as samples to store; and building a convolutional neural network model diagram for identifying contents of gas components, and identifying an atmosphere. The virtual sensor array fabricated by the present disclosure may reduce the array size and the overall volume of a device to an extreme content; the built convolutional neural network may dig other feature information besides a response value from a response curve of a sensor, thereby effectively improving identification efficiency and identification accuracy.

9 Claims, 7 Drawing Sheets

METHOD FOR DETECTING AN AIR DISCHARGE DECOMPOSED PRODUCT BASED ON A VIRTUAL SENSOR ARRAY

FIELD

Embodiments of the present disclosure generally relate to a method for detecting an air discharge decomposed product, and more particularly relate to a method for detecting an air discharge decomposed product based on a virtual sensor array.

BACKGROUND

As a natural insulating medium, air is widely applied to power equipment (e.g., a distribution switchgear). Air-insulated power facilities are extensively used in a power system, such that their reliable operation is of a great significance to grid safety. Prior researches have found that $NO_2$, CO and $O_3$ are the three main decomposed products from discharge failure of air-insulated power facilities, and faults of the facilities may be early alerted by detecting features of the three gas components. Current common technologies for analyzing $NO_2$, CO and $O_3$, which are featured gases from air discharge decomposition, mainly include gas chromatography and ultraviolet absorption spectrometry, which may implement accurate identification of a hybrid gas; however, relevant detection apparatuses have a complex structure and a high cost, such that they can hardly be applied to online monitoring of the featured decomposed products from air discharge. A nanometer material-based semiconductor gas-sensitive sensor has increasingly gained attention in recent years due to its high sensitivity steady performance, simple fabricating process, low cost, and compatibility with modern electronic devices.

Despite of the varieties of sensors for gas detection, the cross-sensitivity issue is always a restraint for their development. In recent years, it has become a common thinking to construct an array based on a plurality of sensors of different sensitivities so as to solve the cross-sensitivity issue. However, to detect the contents of a plurality of components of a hybrid gas, the array scale as needed increases accordingly, thereby bringing about the deficiencies such as a large size, a complex structure, and a high cost. Moreover, to reach an appropriate operating temperature, a certain heating voltage needs to be applied to the sensors, which causes more power consumption of the sensors. Furthermore, traditional identification algorithms only use response values of the sensor array as feature input quantities, such that the feature values obtained are relatively few, and other important information of the hybrid gas features included in a response curve are always missed; besides, it is time-consuming and strenuous to extract such feature values.

SUMMARY

To address the issue of identifying contents of components of a decomposed product from discharge of an air-insulated power facility, the present disclosure provides a method for detecting an air discharge decomposed product based on a virtual sensor array, to address the issue of high power consumption of traditional gas sensor arrays, the present disclosure provides a pulse heating voltage approach, which may significantly reduce power consumption of sensors compared with a constant heating voltage approach; to address the issue of large size of a large scale sensor array, the present disclosure takes each different temperature point as a "virtual" sensor based on temperature features of sensors so as to provide enough data amount with a relatively small physical scale of the array; and to address the drawback of small feature extraction amount in traditional identification algorithms, the present disclosure provides a fully data driven identification method based on a convolutional neural network so as to mitigate the impact of artificially extracted feature quantity on identification precision.

To achieve the objects above, the present disclosure provides a method for detecting an air discharge decomposed product based on a virtual sensor array, comprising:

Step S100: fabricating a virtual sensor array:

Step S200: disposing the virtual sensor array in a hermetically sealed gas chamber, energizing, and initializing;

Step S300: performing gas-sensitive testing to the virtual sensor array and storing a testing result as samples to store; and Step S400: building a convolutional neural network model diagram for identifying contents of gas components, and identifying an atmosphere.

Further, the step S100 comprises:

Step S101: fabricating a sensor base: fabricating a devised electrode pattern on a sensor substrate, and leading out a corresponding electrode lead; wherein the electrode pattern is formed on a surface of the sensor substrate by an electronic beam evaporation process and a photolithographic process, and respective electrode pairs are crossed like a brush, but do not intersect;

Step S102: applying nanometer gas-sensitive materials: uniformly applying different nanometer gas-sensitive materials on the surface of the sensor base to form an entity array; further, sufficiently dispersing the nanometer gas-sensitive materials into ethanol, and coating a surface of a front-side testing electrode with the materials by spraying, spin-coating, or drop-coating to form a gas-sensitive film.

Step S103: forming a virtual sensor array: applying a pulse heating voltage to the entire sensor array to form the virtual sensor array.

Further, the virtual sensor array comprises: a sensor substrate, electrodes, and nanometer gas-sensitive materials, the sensor substrate and the electrodes forming the sensor base, the electrodes including a front-side testing electrode and a back-side heating electrode; the nanometer gas-sensitive materials being applied on the front-side testing electrode.

Further, the front-side testing electrode is configured for testing gas-sensitive resistance, and a fabricating material thereof includes any one of gold-nickel, platinum, and silver-palladium.

Further, a thickness of the front-side testing electrode is 50~300 nm.

Further, the back-side heating electrode is configured for applying different pulse heating voltages to perform thermal processing to the sensor array, and a fabricating material thereof includes any one of gold-nickel and platinum.

Further, a thickness of the back-side heating electrode is 50~300 nm.

Further, the nanometer gas-sensitive material includes any one of tin oxide, titanium oxide, zinc oxide, indium oxide, cerium oxide, tungsten oxide, nickel oxide and cobalt oxide, and an application thickness is 100 nm~1 μm.

Further, the pulse includes: a square wave, a sine wave, and a triangular wave.

Further, the step S400 comprises:

Step S401: creating an input matrix and an output vector, where a two-dimensional measurement matrix formed by the number of virtual sensor arrays and a response time sequence is taken as the input matrix, and contents of the gas components are taken as the output vectors;

Step S402: building and training a fully data-driven convolutional network model;

Step S403: identifying components of a hybrid gas using the trained convolutional network model.

The present disclosure brings about the following advantageous effects:

1. Compared with the constant voltage heating mode, the pulse voltage heating mode employed by the present disclosure has less power consumption, and the response results include more response information.

2. The virtual sensor array fabricated by the present disclosure may significantly reduce the array size, thereby reducing the bulk size of the device.

3. The convolutional neural network built by the present disclosure may dig other feature information besides response values from a response curve of a sensor, thereby effectively improving identification efficiency and identification accuracy.

DETAILED DESCRIPTION OF EMBODIMENTS

Hereinafter, embodiments of the present disclosure will be described in detail with reference to the accompanying drawings. It is noted that the embodiments of the present disclosure are only part of embodiments, which shall not constitute a limitation to the present disclosure.

Figure 1:
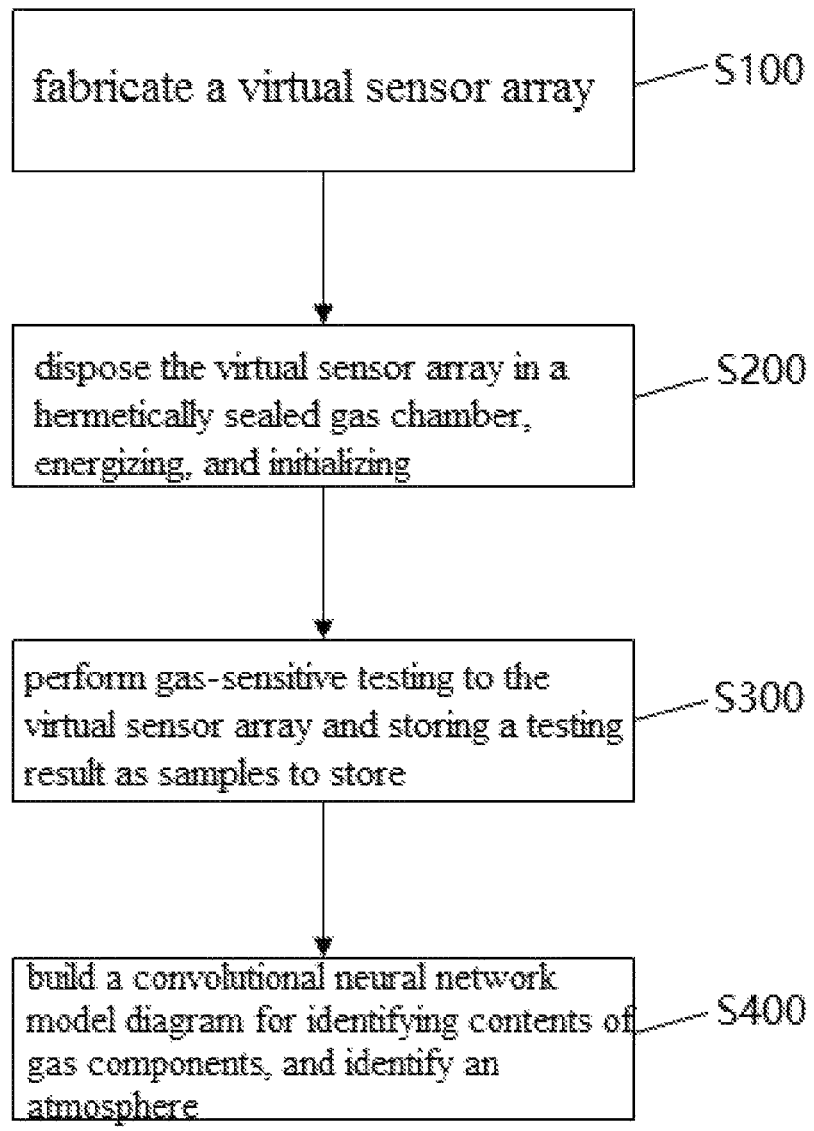
FIG. 1 is a flow diagram of a method for detecting an air discharge decomposed product based on a virtual sensor array according to an embodiment of the present disclosure.

As shown in FIG. 1, the present disclosure provides a method for detecting an air discharge decomposed product based on a virtual sensor array, comprising:

Step S100: fabricating a virtual sensor array;

Step S200: disposing the virtual sensor array in a hermetically sealed gas chamber, energizing, and initializing;

Step S300: performing gas-sensitive testing to the virtual sensor array and storing a testing result as samples to store; and Step S400: building a convolutional neural network model diagram for identifying contents of gas components, and identifying an atmosphere.

Figure 2:
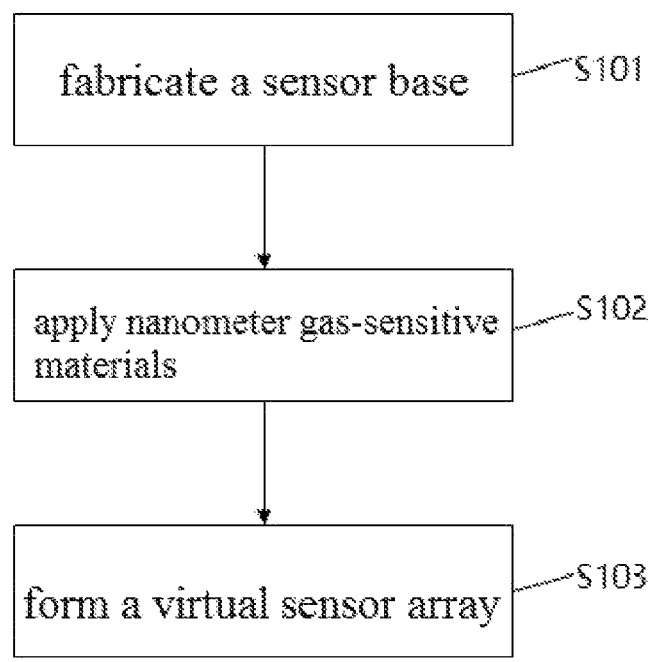
FIG. 2 is a flow diagram of a method for fabricating a virtual sensor array according to an embodiment of the present disclosure.

In a specific embodiment of the step S100, as shown in FIG. 2, a method of fabricating a sensor array comprises:

Step S101: fabricating a sensor base: fabricating a devised electrode pattern on a sensor substrate, and leading out a corresponding electrode lead, wherein the electrode pattern is formed on a surface of the sensor substrate by an electronic beam evaporation process and a photolithographic process, and respective electrode pairs are crossed like a brush, but do not intersect;

Step S102: applying nanometer gas-sensitive materials: uniformly applying different nanometer gas-sensitive materials on the surface of the sensor base to form an entity array; further, sufficiently dispersing the nanometer gas-sensitive materials into ethanol, and coating a surface of a front-side testing electrode with the materials by spraying, spin-coating, or drop-coating to form a gas-sensitive film;

Step S103: forming a virtual sensor array: applying a pulse heating voltage to the entire sensor array to form the virtual sensor array.

Figure 3:
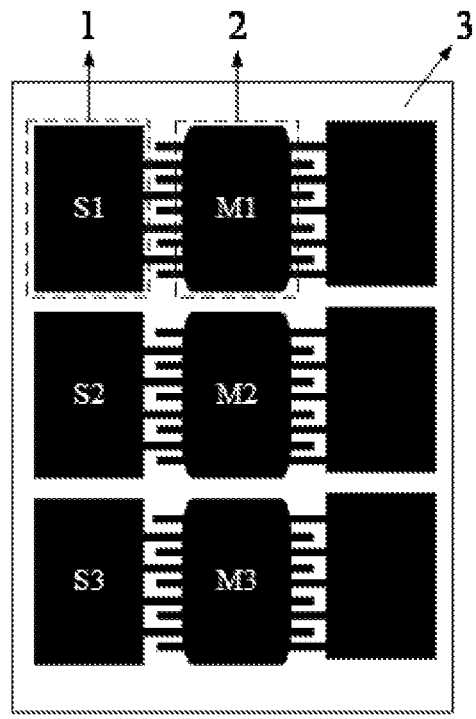
FIG. 3(a) is a front view of a structural diagram of a sensor array according to an embodiment of the present disclosure.
FIG. 3(b) is a rear view of a structural diagram of a sensor array according to an embodiment of the present disclosure; front-side testing electrode—1; nanometer gas-sensitive material—2; sensor substrate—3; and back-side heating electrode—4.
Figure 3B:
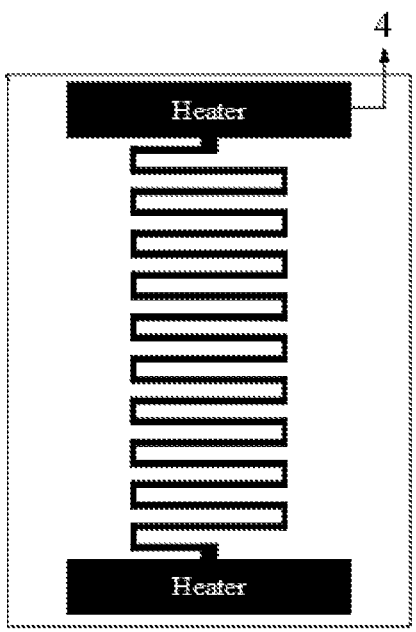

As shown in FIG. 3(a) and FIG. 3(b), the virtual sensor array fabricated according to the embodiment above comprises: a sensor substrate 3, electrodes, and nanometer gas-sensitive materials 2, the sensor substrate 3 and the electrodes forming the sensor base, the electrodes including a front-side testing electrode 1 and a back-side heating electrode 4. Particularly, the front-side testing electrode 1 is configured for testing gas-sensitive resistance, a fabricating material of which may be selected from any one of gold-nickel, platinum, and silver-palladium, with a thickness of 50~300 nm and a width and interval of 20~200 um, the back-side heating electrode 4 is configured for applying different pulse heating voltages to the sensor array for thermal processing to thereby construct a virtual sensor array; a fabricating material of the back-side heating electrode may be selected from gold-nickel or platinum, with a thickness of 50~300 nm, and a width and interval of 20~200 um; the nanometer gas-sensitive material 2 is applied onto the front-side testing electrode 1, which may be made from any of tin oxide ($SnO_2$), titanium oxide ($TiO_2$), zinc oxide (ZnO), indium oxide ($In_2O_3$), cerium oxide ($CeO_2$), tungsten oxide ($WO_3$), nickel oxide (NiO) or cobalt oxide ($Co_2O_3$), with an application thickness of 100 nm~1 μm.

The pulse may be a square wave, a sine wave, or a triangular wave, which enables a temperature adjustment in a range from room temperature 25° C. to 300° C. Different response results for the same entity sensor may be obtained by periodically changing heating voltage amplitudes.

During a specific implementation process, as shown in FIG. 3(a) and FIG. 3(b), the sensor array includes 3 entity sensors; the front-side testing electrode 1 preferably uses gold as the fabricating material with a thickness of 100 nm, the inter-electrode interval and the width being both 100 μm, the back-side heating electrode 4 preferably adopts platinum as the fabricating material, with a thickness of 100 nm, and the inter-electrode interval and the width being both 100 μm. The nanometer gas-sensitive materials are preferably selected from a group consisting of Tin oxide ($SnO_2$), nickel oxide (NiO), tungsten oxide ($WO_3$), which are uniformly applied to different material areas on the surface of the array by spraying, the thickness of the film being 300 nm.

Figure 4:
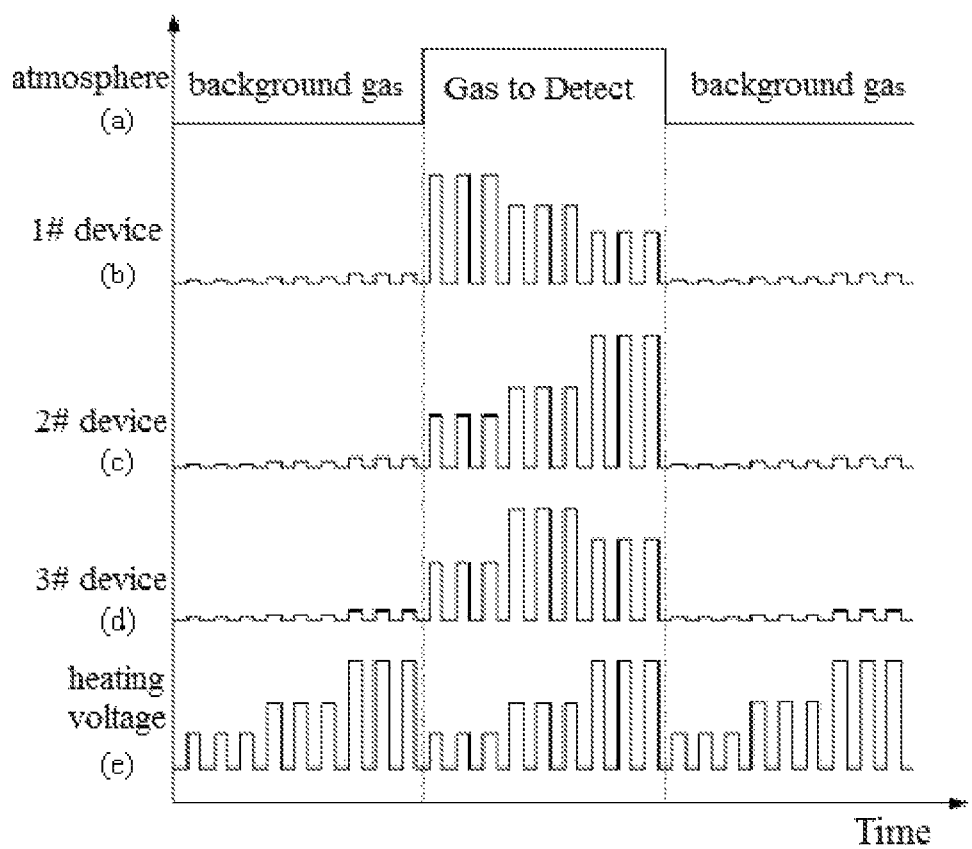
FIG. 4 is a schematic diagram of a pulse heating voltage waveform and a virtual sensor array response in an embodiment of the present disclosure.

During a specific implementation process, a virtual sensor array is formed by applying pulse square wave heating voltages of different amplitudes to the sensor array, as shown in FIG. 4, where the pulse heating voltage amplitudes are controlled in a range from 20 mV to 2V, with a period of 5~10 s, and a heating power loss of 10~60 mW. The pulse heating voltage amplitude changes once every 3 periods, such that there are three amplitudes in total. In this way, an array including 9 pieces of virtual sensor response information is created.

Figure 5:
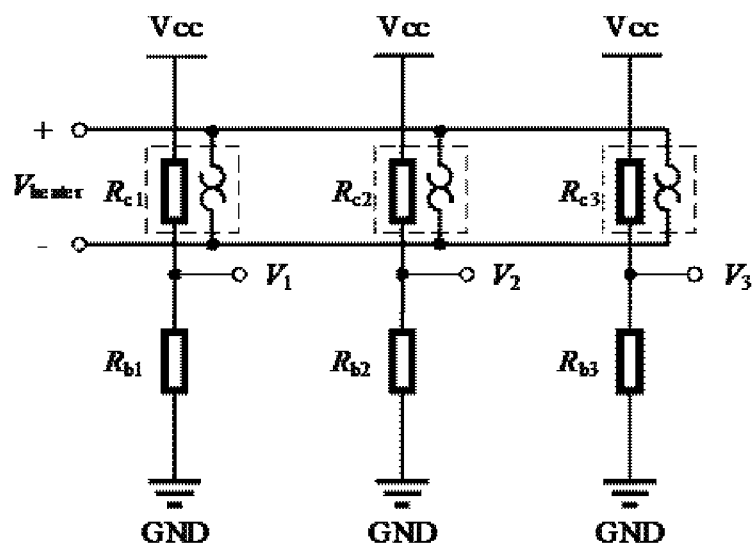
FIG. 5 is a schematic diagram of a sensor array signal acquiring circuit according to an embodiment of the present disclosure.

In the specific implementation manner of the step S200, the sensor array is arranged in a hermetically sealed gas chamber with a volume of 800 mL, and the atmospheric environment in the gas chamber is switched by dynamical gas distribution. It needs to be noted that in this embodiment, the atmosphere refers to a hybrid gas obtained by mixing a plurality of gases according to different ratios. FIG. 5 shows a sensor array response signal acquiring circuit, where a corresponding wiring terminal is led out from the gas chamber, such that the sensor gas-sensitive resistors $R_{ci}$ are serially connected to a standard resistor $R_{bi}$; by applying a 5V voltage at two ends, changes of the gas-sensitive resistors $R_{ci}$ may be calculated by testing the sensor response signal V1. The sensor response value S is defined as a relative change quantity of the nanometer gas-sensitive film resistance:

$$S = \frac{\Delta R}{R} = \frac{R_a - R_g}{R_a} \times 100\% \qquad (1)$$

where $R_a$ represents a resistance value of the sensor in the background atmosphere, and $R_g$ represents a resistance value of the sensor in the target atmosphere.

After layout of the sensor array is completed, it is energized and initialized; and whether the NI-USB-6218 data acquisition card may transmit the signal $V_i$ to an upper computer is tested.

During the specific implementation process of the step S300, kind classification and concentration identification are performed to, for example, a hybrid gas as an air-insulated discharge decomposed product including two typical gases, $NO_2$ and CO, wherein the gas concentration points take 0, 5, 10, 15, and 20 ppm, 25 atmospheric combinations in total, as shown in Table 1:

TABLE 1

| $NO_2$ | CO (ppm) | | | | |
|---|---|---|---|---|---|
| (ppm) | 0 | 5 | 10 | 15 | 20 |
| 0 | (0,0) | (0,5) | (0,10) | (0,15) | (0,20) |
| 5 | (5,0) | (5,5) | (5,10) | (5,15) | (5,20) |
| 10 | (10,0) | (10,5) | (10,10) | (10,15) | (10,20) |
| 15 | (15,0) | (15,5) | (15,10) | (15,15) | (15,20) |
| 20 | (20,0) | (20,5) | (20,10) | (20,15) | (20,20) |

Based on the 25 atmospheric environments as shown in Table 1, the outputs of the sensor array are tested separately, and the array output results are uploaded to the upper computer and stored as a sample set.

Figure 6:
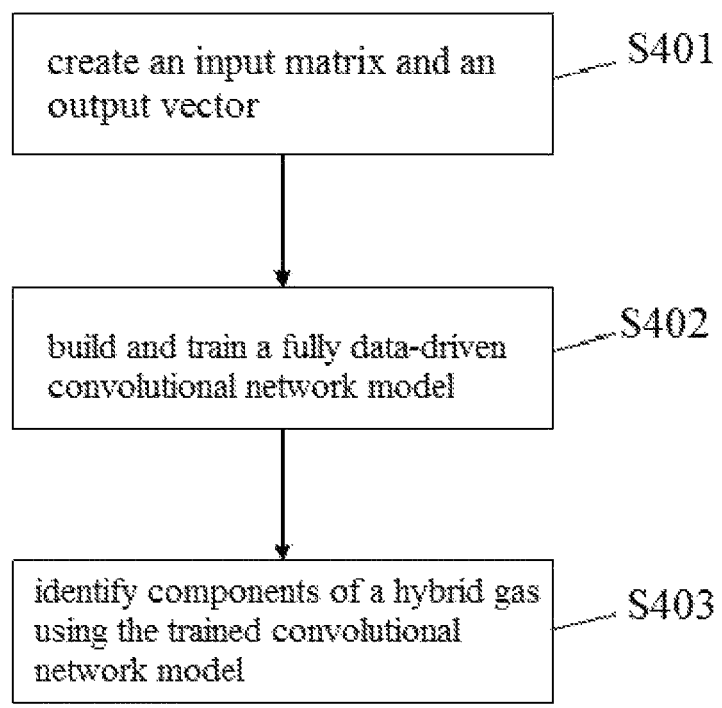
FIG. 6 is a flow diagram of a method for identifying contents of gas components based on a convolutional neural network model according to an embodiment of the present disclosure.
Figure 7:
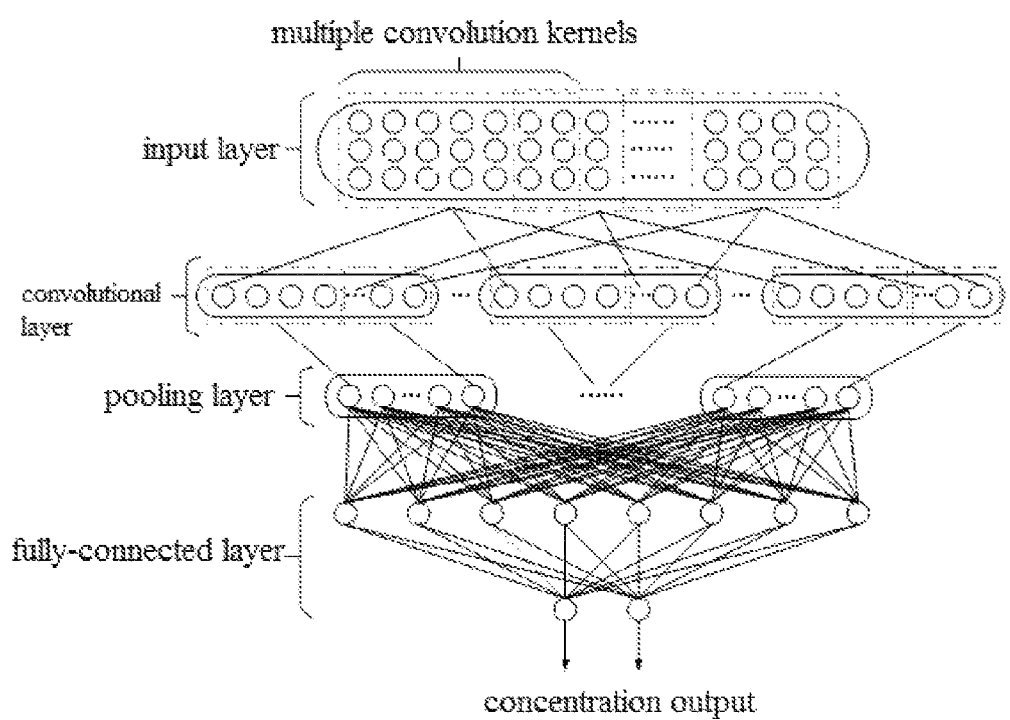
FIG. 7 is a schematic diagram of a convolutional neural network model for identifying contents of gas components according to an embodiment of the present disclosure.

During the specific implementation process of the step S400 as shown in FIG. 7, a convolutional neural network model for identifying contents of gas components is built. Specific building steps are shown in FIG. 6.

Step S401: creating an input matrix and an output vector, where a two-dimensional measurement matrix formed by the number of virtual sensor arrays and a response time sequence is taken as the input matrix, and contents of the gas components are taken as the output vectors;

The two-dimensional measurement matrix is a time sequence matrix, and the response signal of the respective virtual sensor under a specific atmosphere is:

$$S_k = \begin{bmatrix} S_k^{1,1} & \cdots & S_k^{1,d} \\ \vdots & \ddots & \vdots \\ S_k^{p,1} & \cdots & S_k^{p,d} \end{bmatrix} \qquad (2)$$

where $S_k$ denotes the two-dimensional measurement matrix of the $k^{th}$ sample, p denotes the number of virtual sensors, and d denotes the output time sequence length of each virtual sensor.

With output vectors of the contents of the gas components as the output quantity, the equation is:

$$H_k = (H_k^1, \ldots, H_k^m) \qquad (3)$$

where $H_k$ denotes the content of a component of the hybrid gas in the $k^{th}$ sample, and m denotes the kind of a gas.

As a result, a training sample set D may be derived:

$$D = \{(S_k, H_k)\}_{k=1}^{l} \qquad (4)$$

where l denotes the total number of training samples.

The input and output quantities are subjected to normalization processing, resulting in:

$$\left\{ x_k^{p,i} = \frac{S_k^{p,i} - S_{k_{min}}^p}{S_{k_{max}}^p - S_{k_{min}}^p} \right\}_{i=1}^{d} \qquad (5)$$

$$\left\{ y_k^j = \frac{H_k^j - H_{k_{min}}}{H_{k_{max}} - H_{k_{min}}} \right\}_{j=1}^{m} \qquad (6)$$

where $S_k^{p,i}$ denotes a response signal of each virtual sensor before normalization, $x_k^{p,i}$ denotes a response signal of each virtual sensor after the normalization, $S_{k_{min}}^p$ denotes a response signal minimum value of the $k^{th}$ sample, $S_{k_{max}}^p$ denotes a response signal maximum value, $H_k^j$ denotes an output parameter before normalization, $y_k^j$ denotes the normalized output parameter, $H_{k_{min}}$ denotes an output vector minimum value, and $H_{k_{max}}$ denotes the output vector maximum value.

In this way, the normalized sample set D may be derived as:

$$D = \{(x_k, y_k)\}_{k=1}^{l} \qquad (7)$$

Step S442: building a fully data-driven convolution network model; as shown in FIG. 5, the convolutional network model comprises 1 convolutional layer and 1 pooling layer; the fully connected layer comprises 1 hidden layer and 1 output layer; a process of training the convolution network model is provided below:

(A) Building a Convolutional Layer

The input sample matrix $S_k$ has a size of p×d, the number of convolution kernels is n, the size of each convolution kernel is p×m, and the sliding step size is t. For the convolutional neural network, the convolution kernels corresponding to each layer are identical; then, the size of the output feature matrix corresponding to each convolution kernel is 1×[(d−m)/t+1]. Each element z in the output feature matrix of the $r^{th}$ convolution kernel may be represented as.

$$z = f\left(\sum_{i=1}^{p \cdot m} w_i^r \cdot s_k + b^r\right) \quad (8)$$

where w denotes respective elements in the convolution kernel, and b denotes a bias amount corresponding to each convolution kernel. In the convolutional layer, the number of to-be-trained parameters is n×(p·m+1).

where f denotes an activation function, which selects a linear rectifying function, denoted as:

$$f(x) = \begin{cases} 0, & x < 0 \\ x, & x \geq 0 \end{cases} \quad (9)$$

(B) Building a Pooling Layer

Let the pool size be x, guaranteeing that x may be exactly divisible by 1×[(d−m)/t+1]; then, the size of the output feature matrix corresponding to the pooling layer is 1×[(d−m)/t+1]/x. The convolutional layer is subjected to down-sampling processing using the maximum pooling method; then, each element a in the pooling layer may be represented as:

$$a_j = \max_{c=1}^{x}\{z_{j,c}\} \quad (10)$$

where j denotes the pool number, and c denotes the element number in each pool.

(c) Building a Full, Connected Layer

The output feature matrix obtained from the pooling layer is inputted in the lower-layer neuron by full connection, and the whole network is trained using an error back-propagation algorithm. The process is provided below;

i. defining a learning rate $\eta \in (0,1)$, and randomly initializing all connection rights and thresholds in the neural network.

ii. computing a neural network output $\hat{y}_k^j$:

$$\hat{y}_k^i = \frac{1}{1 + e^{-(\beta_j - \theta_j)}} \quad (11)$$

$$\beta_i = \Sigma_{h=1}^{q} \omega_{hj} b_h \quad (12)$$

$$b_h = \frac{1}{1 + e^{-(\alpha_h - \gamma_h)}} \quad (13)$$

$$a_h = \Sigma_{i=1}^{d} v_{ih} s_k^i \quad (14)$$

where, $\alpha_h$ denotes input of the $n^{th}$ neuron at the hidden layer, $b_h$ denotes output of the $h^{th}$ neuron at the hidden layer, $\beta_1$ denotes input of the $j^{th}$ output neuron at the hidden layer, $\gamma_h$ denotes the threshold of the $h^{th}$ neuron at the hidden layer, $\theta_j$ denotes the threshold of the $j^{th}$ neuron at the output layer, $v_{ih}$ denotes a connection right between the $i^{th}$ neuron at the output layer and the $h^{th}$ neuron at the hidden layer, $\omega_{h_1}$ denotes a connection right between the $h^{th}$ neuron at the hidden layer and the $j^{th}$ neuron at the output layer, d denotes the quantity of neurons at the input layer, and q denotes the quantity of neurons at the hidden layer.

iii. calculating the gradient terms $g_j$ of the neurons at the output layer:

$$g_1 = \hat{y}_k^i(1-\hat{y}_k^j)(y_k^j - \hat{y}_k^j) \quad (15)$$

iv. calculating the gradient terms $e_h$ of the neurons at the hidden layer $$\epsilon_h = b_h(1 - b_h)\sum_{j=1}^{m} \omega_{hj} g_j \quad (16)$$

where $b_h$ denotes an output of the $h^{th}$ neuron at the hidden layer, $\omega_{h_j}$ denotes a connection right between the $h^{th}$ neuron at the hidden layer and the $j^{th}$ neuron at the output layer, $g_j$ denotes a gradient term of a neuron at the output layer, and m denotes the quantity of neurons at the output layer.

v. training the neuron network based on the calculated gradient terms of the neurons at the output layer and the hidden layer, including.

updating the connection rights of the neurons of the output layer and the hidden layer.

$$\omega'_{h_j} = \omega_{hj} + \Delta\omega_{hj} = \omega_{hj} + \eta g_j b_h \quad (17)$$

$$v'_{ih} = v_{ih} + \Delta v_{ih} = v_{ih} + \eta e_h x_k^i \quad (18)$$

updating the thresholds of the neurons at the output layer and the hidden layer:

$$\theta'_j = \theta_j + \Delta\theta_j = \theta_j - \eta g_j \quad (19)$$

$$\gamma'_h = \gamma_h + \Delta\gamma_h = \gamma_h - \eta e_h \quad (20)$$

Vi. calculating an accumulated error in the training set D:

$$E_k = \frac{1}{2}\Sigma_{j=1}^{m}(\hat{y}_j^k - y_j^k)^2 \quad (21)$$

$$E = \frac{1}{2}\Sigma_{k=1}^{l} E_k \quad (22)$$

The ultimate goal of the algorithm is to minimize the accumulated error E of the training set D. Compare the network calculated output $\hat{y}_l^k$ and the actual output $y_l^k$; if the accumulated error reaches a precision requirement, stop training the neural network and enter the testing phase.

Step S403: identifying components of the hybrid gas using the trained convolutional network model.

Identifying components of the hybrid gas refers to testing the contents of the components of the hybrid gas based on the established convolutional neural network identification model, the specific process of which is shown below.

(a) acquiring samples based on the virtual sensor array to establish a testing set T:

$$T = \{(S_k, H_k)\}_{k=1}^{n} \quad (23)$$

where n denotes the number of samples in the testing set.

(b) testing the trained gas identification network model using the training set to check accuracy of the model.

In this embodiment, the acquired sample set serves as the training set, and the contents of the components of the hybrid atmosphere are identified in conjunction with the gas identification model based on the convolutional neural network. To identify the contents of the hybrid gas including $NO_2$—Co, 20 groups of response results are acquired through a gas-sensitive experiment under 25 atmospheric environments based on the virtual sensor array, as shown in Table 2.

TABLE 2

| Testing sample | Actual concentration (ppm) | | Calculated concentration (ppm) | | Error (%) | |
|---|---|---|---|---|---|---|
| | NO2 | CO | NO2 | CO | NO2 | CO |
| 1 | 0 | 20 | 0.13 | 20.73 | — | 3.7 |
| 2 | 5 | 15 | 4.77 | 14.42 | 4.6 | 3.9 |
| 3 | 10 | 10 | 10.23 | 10.26 | 2.3 | 2.6 |
| 4 | 15 | 5 | 14.75 | 5.13 | 1.7 | 2.6 |
| 5 | 20 | 0 | 20.31 | 0.20 | 1.6 | — |

It may be seen from the identification results of the 5 samples in Table 2 that, the sensor array according to the present disclosure enables a relatively accurate identification of the contents of the components of the hybrid gas including NO2 and Co. Compared with existing approaches, the virtual sensor array according to the present disclosure in conjunction with the fully data-driven convolutional neural network may not only identify the contents of the components of the hybrid gas but also has an online monitoring potential, which lays a solid foundation for fault alert of the air-insulated power facilities.

The present disclosure adopts specific embodiments to illustrate the principle and implementation manners of the present disclosure; the illustration of the embodiments is only for facilitating of understanding the usage and core idea of the present disclosure. The present disclosure may be altered in respect of the specific implementation manners and the application scope dependent on actual conditions, and the embodiments above do not limit the application scope of the present disclosure. Any addition, transformation, or equivalent substitution in the art to the technical features should all fall within the protection scope of the present disclosure without departing from the technical features provided by the technical solutions of the present disclosure.

What is claimed is:

1. A method for detecting an air discharge decomposed product based on a virtual sensor array, comprising:
    Step S100: fabricating a virtual sensor array;
    Step S200: disposing the virtual sensor array in a hermetically sealed gas chamber, energizing, and initializing;
    Step S300: performing gas-sensitive testing to the virtual sensor array and storing a testing result as samples to store; and
    Step S400: building a convolutional neural network model diagram for identifying contents of gas components and identifying an atmosphere
    wherein the step S100 comprises:
    Step S101: fabricating a sensor base: fabricating a devised electrode pattern on a sensor substrate, and leading out a corresponding electrode lead; wherein the electrode pattern is formed on a surface of the sensor substrate by an electronic beam evaporation process and a photo-lithographic process, and respective electrode pairs are crossed like a brush, but do not intersect;
    Step S102: applying nanometer gas-sensitive materials: uniformly applying different nanometer gas-sensitive materials on the surface of the sensor base to form an entity array; further, sufficiently dispersing the nanometer gas-sensitive materials into ethanol, and coating a surface of a front-side testing electrode with the materials by spraying, spin-coating, or drop-coating to form a gas-sensitive film;
    Step S103: forming a virtual sensor array: applying a pulse heating voltage to the entire sensor array to form the virtual sensor array.

2. The method according to claim 1, wherein the virtual sensor array comprises: a sensor substrate, electrodes, and nanometer gas-sensitive materials, the sensor substrate and the electrodes forming a sensor base, the electrodes including a front-side testing electrode and a back-side heating electrode, the nanometer gas-sensitive material being applied on the front-side testing electrode.

3. The method according to claim 2, wherein the front-side testing electrode is configured for testing a gas-sensitive resistance, and a fabricating material includes any one of gold-nickel, platinum, and silver-palladium.

4. The method according to claim 3, wherein a thickness of the front-side testing electrode is 50~300 nm.

5. The method according to claim 2, wherein the back-side heating electrode is configured for applying different pulse heating voltages to perform thermal processing to the sensor array, and a fabricating material thereof includes any one of gold-nickel and platinum.

6. The method according to claim 5, wherein a thickness of the back-side heating electrode is 50~300 nm.

7. The method according to claim 2, wherein the nanometer gas-sensitive material includes any one of tin oxide, titanium oxide, zinc oxide, indium oxide, cerium oxide, tungsten oxide, nickel oxide and cobalt oxide, and an application thickness is 100 nm~1 μm.

8. The method according to claim 1, wherein the pulse includes: a square wave, a sine wave, and a triangular wave.

9. The method according to claim 1, wherein the step S400 comprises:
    Step S401: creating an input matrix and an output vector, where a two-dimensional measurement matrix formed by the number of virtual sensor arrays and a response time sequence is taken as the input matrix, and contents of the gas components are taken as the output vectors;
    Step S402: building and training a fully data-driven convolutional network model;
    Step S403: identifying components of a hybrid gas using the trained convolutional network model.

* * * * *